(12) United States Patent
Embrey et al.

(10) Patent No.: US 9,314,622 B2
(45) Date of Patent: Apr. 19, 2016

(54) FUNCTIONAL ELECTRICAL STIMULATION (FES) METHOD AND SYSTEM TO IMPROVE WALKING AND OTHER LOCOMOTION FUNCTIONS

(71) Applicant: Good Samaritan Hospital, Puyallup, WA (US)

(72) Inventors: David G. Embrey, Puyallup, WA (US); Jeffrey Stonestreet, Gig Harbor, WA (US); Gadi Alon, Rockville, MD (US)

(73) Assignee: GOOD SAMARITAN HOSPITAL, Puyallup, WA (US)

( * ) Notice: Subject to any disclaimer, the term of this patent is extended or adjusted under 35 U.S.C. 154(b) by 0 days.

(21) Appl. No.: 13/879,557

(22) PCT Filed: Oct. 25, 2012

(86) PCT No.: PCT/US2012/061806
§ 371 (c)(1),
(2) Date: Apr. 15, 2013

(87) PCT Pub. No.: WO2013/063200
PCT Pub. Date: May 2, 2013

(65) Prior Publication Data
US 2014/0128939 A1     May 8, 2014

Related U.S. Application Data

(60) Provisional application No. 61/552,865, filed on Oct. 28, 2011.

(51) Int. Cl.
*A61N 1/36*     (2006.01)
*A61N 1/372*     (2006.01)
(Continued)

(52) U.S. Cl.
CPC ........ *A61N 1/36003* (2013.01); *A61N 1/36014* (2013.01); *A61N 1/37252* (2013.01);
(Continued)

(58) Field of Classification Search
CPC ............ A61N 1/0452; A61N 1/36003; A61N 1/36014; A61N 1/36067
USPC ...................................................... 607/48, 49
See application file for complete search history.

(56) References Cited

U.S. PATENT DOCUMENTS 5,167,229 A * 12/1992 Peckham et al. ................. 607/48
5,814,093 A * 9/1998 Stein ............................... 607/49
(Continued)

OTHER PUBLICATIONS

"Acland's Video Atlas of Human Anatomy." Nerves of the Leg and Ankle 2.3.11. Wolters Kluwer. Web. Jun. 19, 2015. <https://aclandanatomy.com/abstract/4010444>.*
(Continued)

*Primary Examiner* — Allen Porter, Jr.
(74) *Attorney, Agent, or Firm* — Birch, Stewart, Kolasch & Birch, LLP

(57) ABSTRACT

A method and system which provides wireless, noninvasive electrical stimulation to different muscle groups to allow the user to conduct physical activities, such as walking, by stimulating various muscle groups in the body at the correct times of activation or by stimulating muscle groups in a simulation mode when standing, sitting or lying down, whereby walking is not required to stimulate the various muscle groups. The system provides a small portable wearable system which utilizes available software, including Bluetooth technology, to provide electrical nerve stimulating pulses with low current, minimal phase charge which is controlled remotely and induce desired muscle contraction with increased comfort for the user. The present method and system applies electrical stimulation with accurate timing, based on a three-dimensional motion sensor, as a trigger to initiate stimulation and which is adapted to turn itself on and off when not walking.

26 Claims, 9 Drawing Sheets

(51) Int. Cl.
  *A61B 5/11* (2006.01)
  *A61N 1/04* (2006.01)
  *A61B 5/00* (2006.01)

(52) U.S. Cl.
  CPC .............. *A61B 5/112* (2013.01); *A61B 5/4836* (2013.01); *A61B 5/6828* (2013.01); *A61B 2562/0219* (2013.01); *A61N 1/0452* (2013.01); *A61N 1/0476* (2013.01)

(56) References Cited

U.S. PATENT DOCUMENTS

| | | | |
|---|---|---|---|
| 7,756,585 B2* | 7/2010 | Embrey et al. ................... | 607/49 |
| 7,844,339 B2 | 11/2010 | Buchner | |
| 2002/0026103 A1* | 2/2002 | Norris ................... | A61B 5/0031 |
| | | | 600/300 |
| 2002/0165590 A1* | 11/2002 | Crowe et al. ................... | 607/48 |
| 2004/0088025 A1* | 5/2004 | Gesotti ........................... | 607/49 |
| 2007/0032841 A1 | 2/2007 | Urmey | |
| 2007/0203533 A1* | 8/2007 | Goren ...................... | A61N 1/32 |
| | | | 607/49 |
| 2009/0043357 A1* | 2/2009 | Tong et al. ...................... | 607/49 |
| 2010/0004715 A1 | 1/2010 | Fahey | |
| 2010/0198102 A1* | 8/2010 | Moore .......................... | 600/554 |
| 2011/0137375 A1* | 6/2011 | McBride ............ | A61N 1/36003 |
| | | | 607/49 |
| 2013/0123568 A1* | 5/2013 | Hamilton et al. ............... | 600/13 |

OTHER PUBLICATIONS

"Acland's Video Atlas of Human Anatomy." Foot Evertor and Invertor Muscles 2.3.8. Wolters Kluwer. Web. Jun. 19, 2015. <https://aclandanatomy.com/abstract/4010436>.*

Alon, G. et al., "Tolerance and Conditioning to Neuro-Muscular Electrical Stimulation Within and Between Sessions and Gender," Journal of Sports Science and Medicine, vol. 4, 2005, pp. 395-405.

International Search Report issued in PCT/US2012/061806 mailed Mar. 13, 2013.

Kantor, G. et al., "Phase Charge Significance in Peripheral Nerve Excitation with Constant Voltage and Constant Current Stimulation," Engineering in Medicine and Biology Society, 1993.

Written opinion of the International Searching Authority issued in PCT/US2012/061806 mailed Mar. 13, 2013.

* cited by examiner

NORMAL GAIT

STEPPAGE GAIT

FOOT DRAG GAIT

FUNCTIONAL ELECTRICAL STIMULATION (FES) METHOD AND SYSTEM TO IMPROVE WALKING AND OTHER LOCOMOTION FUNCTIONS

CROSS-REFERENCE TO RELATED APPLICATIONS

This application is the National Phase of PCT/US2012/061806 filed on Oct. 25, 2012, which claims priority under 35 U.S.C. 119(e) to U.S. provisional application 61/552,865, filed on Oct. 28, 2011, the entire contents of which are hereby expressly incorporated by reference into the present application.

FIELD OF THE INVENTION

The present invention relates generally to a method and a system for non-invasive wearable functional electrical stimulation to augment function of muscles and joints during gait and other locomotion functions. More particularly, the present invention relates to a method and a system for electrically induce contraction in muscles crossing the ankle, knee, hip, and trunk of a person with impaired ability to walk, climb stairs and lifting objects in order to effect improvement in the person's ability to perform these daily functions.

DESCRIPTION OF RELATED ART

A variety of injuries, illnesses and diseases can cause an individual to lose partial or total control of their muscles, making activities such as walking difficult or impossible. For instances, there are over four million adults with impairments due to stroke in the United States. An estimated 500,000 Americans have cerebral palsy and 6,000 babies are born each year in the United States with cerebral palsy. In addition, there are at least 5 million people in the USA who suffer from lower extremity peripheral arterial disease that impair their ability to walk. The limited ability to walk significantly impairs the ability of these individuals to maneuver in their homes, at work, and in recreation. Many other individuals have impaired walking skills due to spina bifida, muscular dystrophy, Parkinson's disease, multiple sclerosis, spinal cord injury, Downs' Syndrome, idiopathetic toe walking, and peripheral neuropathies. Functional Electrical Stimulation (FES) applied to key leg muscles has shown improvement of walking abilities for individuals with some of these disorders.

Even when control over muscles is reduced or lost, muscles will still contract when an externally generated electrical stimulation is applied to the nerves leading to these muscles. The use of FES, first called "Electrical Muscle Therapy," was disclosed in U.S. Pat. No. 3,083,712 issued in 1963 to James E. Keegan Jr. The Keegan, Jr. system employed electrical muscle stimulation to lift the foot during the swing phase of walking by applying small electrical currents to the dorsiflexor muscles. Many adults who suffer a stroke develop "drop foot" resulting in an inability to lift the foot (dorsiflex) when stepping forward in the swing phase of walking. This problem could cause these people to trip, fall, or injure themselves. The Keegan, Jr. patent, while addressing the problem of diminished ability to activate the dorsiflexor muscles offers no disclosure of how the device could be applied to other muscles that participate in walking.

Over the past four decades, drop foot stimulators have been shown to be beneficial. As disclosed in U.S. Pat. No. 5,814,093 to Stein, and U.S. Pat. No. 7,899,556 to Nathan et al, the improvement appears related to technological improvement in what is known as foot drop FES. However, these more advanced FES devices are limited only to the stimulation of the dorsiflexor muscles. As a result, improvement in walking is limited only to patients whose dorsiflexor muscles are weak or not controlled. Patients who have weakness or unable to control the plantar flexors, quadriceps, hamstrings, hip abductors, hip extensors, abdominals, and back muscles cannot benefit from existing systems. Moreover, drop foot is just one component of the walking deficits of adults and children. For example, adults with stroke do not effectively push on each step because of weakness or inappropriate control of a muscle group known as plantar flexors. About 50% of the acceleration force necessary to maintain walking comes from the plantar flexors. Other conditions such as multiple sclerosis or patients status-post fractures or joint replacement, all involve weakness of various opposing or synergistic muscle groups such as quadriceps/hamstrings, hip abductors/extensors and abdominals/back muscles all of which are critical to control walking.

Other commercially available systems (example: PV-300 by EMPI and RS-4$_i$ by RS Medical) suffer from a number of drawbacks. Such systems utilize stimulators which are very large and heavy which makes them difficult to wear for several hours every day. Also, the stimulator's electrical charge per phase (phase charge) is unnecessarily high, leading in many cases to an uncomfortable sensation of the stimulation. Moreover, presently available wearable stimulators contain only one channel which provides limited value to daily functions such as walking if other muscles are also weak or not activated at the correct timing of daily functions.

In the presently known systems, wires and electrodes are separated from the stimulator making it very difficult for the user to effectively reapply the electrodes and achieve correct activation of the target muscles. The present systems are also primarily applicable to the upper or lower limbs of the user and cannot be applied to those who suffer from weak or incorrect activation of trunk muscles, such as the abdominals.

Other systems which are available have utilized a force sensor which is triggered by a heel contact of one leg to begin the electrical stimulation of nerves for the other leg. Such a system is disclosed in U.S. Pat. No. 7,756,585, the subject matter of which is incorporated herein by reference.

It is an object of the present invention to provide a method and system which provides non-invasive, wearable electrical stimulation to different muscle groups to allow an individual to improve performance of physical activities, such as walking.

It is another object of the invention to provide an electrical stimulation method and system utilizing a three dimensional motion sensor as a trigger to providing electrical stimulation.

It is still another object of the invention to provide electrical stimulation with minimal phase charge needed to induce the desired muscle contraction with increased comfort of the user.

It is yet another object of the invention to provide an electrical stimulation system having a minimal size and low profile thus enabling a self-administered, wearable system to the user.

It is yet another object of the invention to provide a stimulator-motion sensor module that is coupled with non-invasive (surface) electrodes, specifically fabricated from non-metal conductive materials (example: silicon-carbon-microfiber) and a non-adhesive conductive medium (example: water).

A further object of the present invention is to provide a miniaturized, wireless, noninvasive electrical stimulation method and system which is designed to excite, by remote control, peripheral sensory and motor nerves using the least amount of electrical charge per phase needed to obtain clinically relevant contraction of skeletal muscles regardless of muscle size.

A still further object of the present invention is to integrate a motion sensor with a stimulator circuit as a means of automatically triggering the stimulation for walking, stair climbing, or lifting objects or during non-locomotion training.

Yet another object of the present invention is to provide a stimulation system which relies upon user motion, user instruction instructions received from a central control to activate and control the desired stimulation.

These and other objects of the invention will become apparent to one of ordinary skill in the art after reading the disclosure of the invention.

SUMMARY OF THE INVENTION

The present invention is directed to a method and system which provides wireless, wearable noninvasive electrical stimulation to different muscle groups to allow the user to perform physical activities, such as walking, by stimulating various muscle groups in the body at the correct times of desired activation during walking or by stimulating muscle groups in a simulation mode when standing, sitting or lying down, whereby walking is not required to stimulate the various muscle groups.

The present invention provides a small portable system which utilizes available software, including Bluetooth technology, to provide electrical nerve stimulating pulses with low current, minimal phase charge which is controlled remotely to create desired muscle contraction with increased comfort for the user. The present method and system applies electrical stimulation with accurate timing, based on a three-dimensional motion sensor, as a trigger to initiate stimulation and which is adapted to turn itself on and off when not walking.

According to one aspect of the present invention, there is provided a wireless method and system of providing walking assistance and/or training to a person with impaired gait, the method and system comprising a combination of elements and steps for: generating first gait event signals in response to a change of signal by means of motion detection in three dimensions (accelerometer/gyroscope/magnetometer, pressure or sound sensors) within a stimulator.

The method and system of the present invention may additionally include the steps for: generating a motion signal in response to sensed movement of the person; allowing the transmission of electrical stimulation to the muscles in response to the signal; and blocking the transmission of electrical stimulation to the muscles when the signal is absent.

The present method and system may additionally include a sensor for developing an activity signal in response to sensed activity of the person; and a control device that (1) allows the transmission of electrical stimulation to the muscles in response to the activity signal and (2) blocks the transmission of electrical stimulation to the muscles when the activity signal is absent.

DETAILED DESCRIPTION OF PREFERRED EMBODIMENTS

The system of the present invention provides an easy to use wearable FES system based on an electronic infrastructure. Because of the uncomplicated design of the system's modules, the user will be able to quickly and properly apply and remove the system as desired. This will enable individuals with disabilities to selectively wear the system for several hours each day, which will facilitate better walking and other locomotor functions and contribute to re-training of the motor patterns of muscles associated with muscle movement, including walking.

Figure 1:
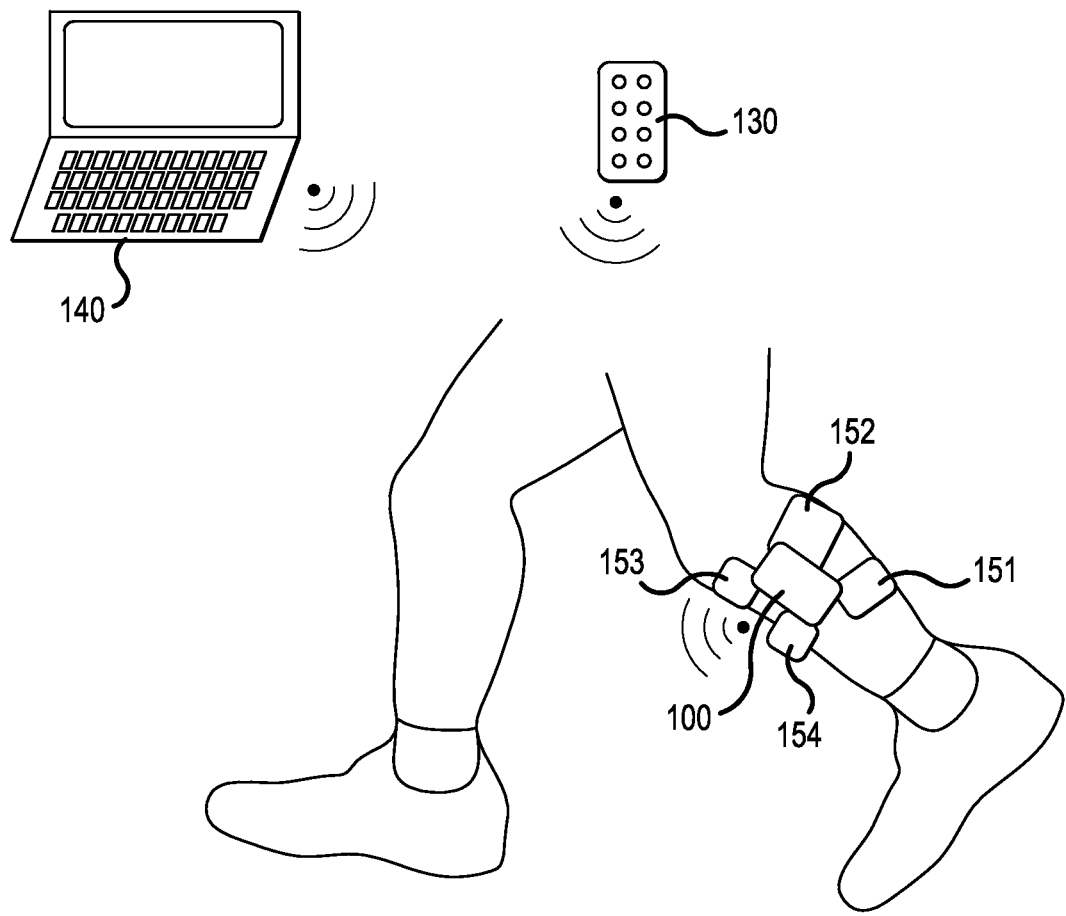
FIG. 1 illustrates the present system applied to the lower leg of a person with unilateral walking impairment.

FIG. 1 shows one application of the present invention and depicts the system applied to the lower leg of the user. Stimulation to the leg is used to control motion of the ankle joint and foot. The stimulator module 100 is secured to the lower leg and electrodes 151-154 are applied to the exterior of the patient so as to be in contact with the user's skin. The stimulator module provides electrical signals to the electrodes in a stimulation pattern, including duration and intensity, according to the desired motion. The stimulator module wirelessly receives signals from either a remote module 130 or an executive module 140. As will be explained in more detail later, the remote module allows a user to initiate the stimulation pattern to be provided to the electrodes without movement of the user and control the intensity of the stimulation.

Figure 2:
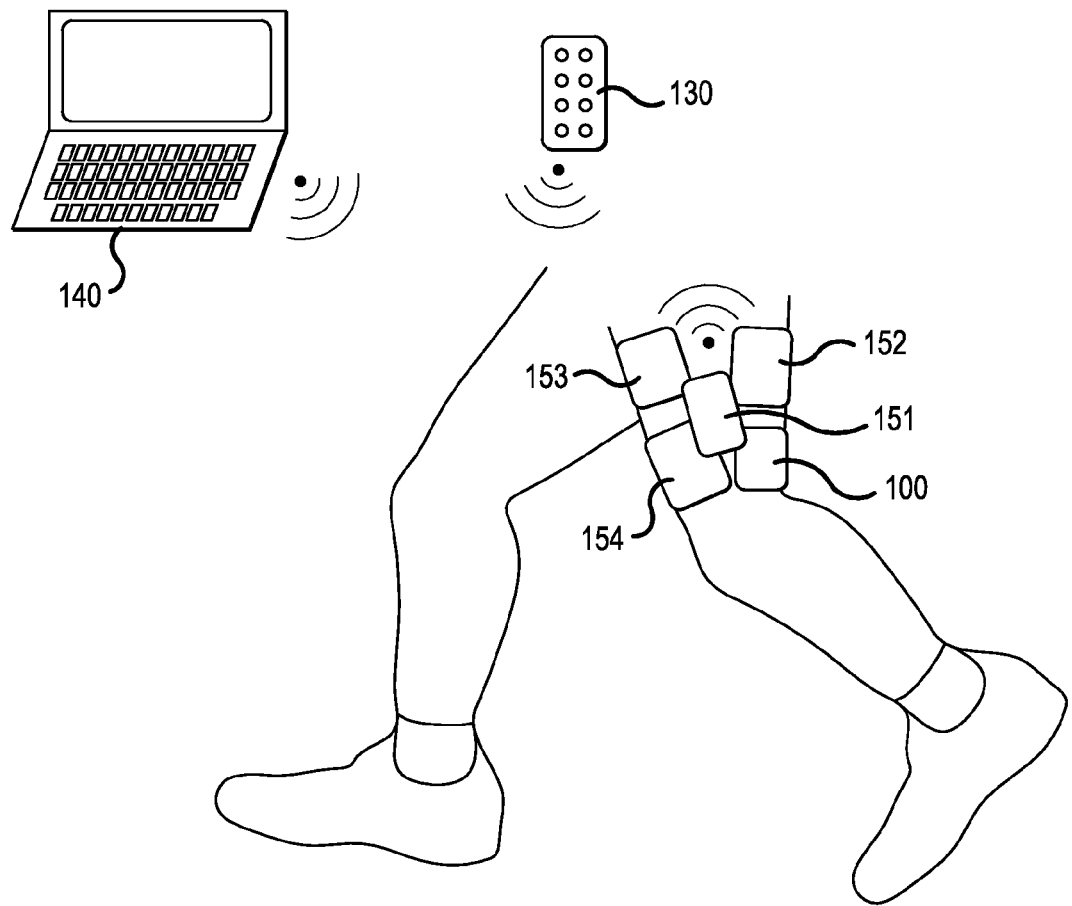
FIG. 2 illustrates the present system applied to the upper leg (thigh) of a person with unilateral walking impairment.

The executive module 140 also allows a clinician to initiate the stimulation pattern to be provided to the electrodes and increase the intensity of the stimulation, and also alter the stimulation pattern created by the stimulator module. In this manner, different patterns may be applied to opposed or synergistic muscle groups to enable different motions, or the stimulator module may be applied to different muscle groups. For instance, FIG. 2 depicts the same stimulator module applied to the upper leg (thigh) of the user. Applying stimulation to the upper leg causes motion of the knee when a proper stimulation pattern is applied to the muscles. The executive module allows a clinician to cause the stimulator module to generate and apply the correct stimulation pattern for the appropriate muscle groups and for the desired activity.

Figure 3A:
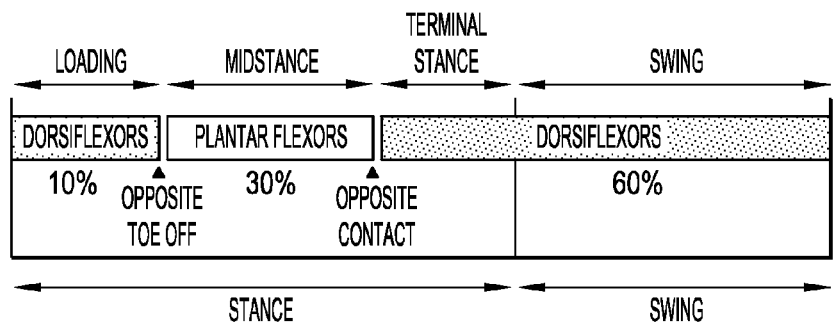
FIGS. 3A-3C are graphical representations of normal timing sequences for activation of the different muscle groups during different activities.
Figure 3B:
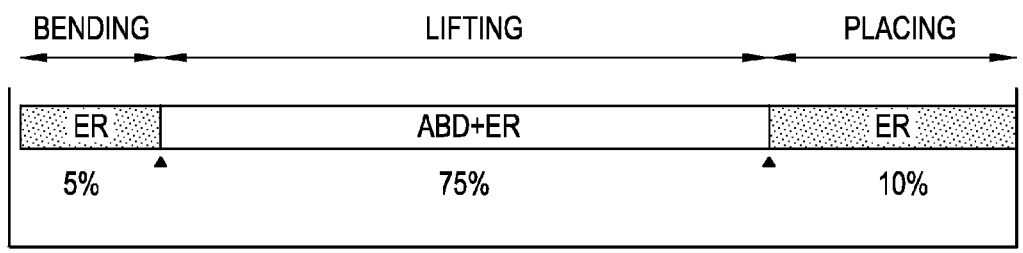
Figure 3C:
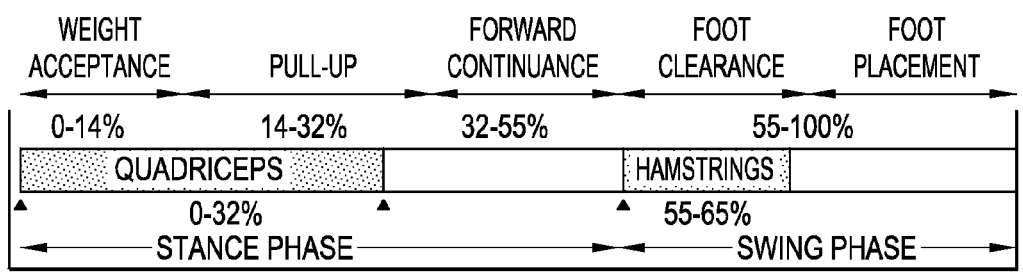

The stimulator module creates different stimulation patterns depending on the muscle groups to which the electrodes are applied and on the desired activity. Stimulation patterns for various opposed or synergistic muscle groups and activities are depicted in FIGS. 3A-3C. FIG. 3A depicts the stimulation pattern, on a time percentage basis, for muscle activation during gait for dorsiflexors and plantar flexors. FIG. 3B depicts the stimulation for desired muscle activation of abdominals and erector spinae. Similarly, FIG. 3C discloses the stimulation pattern, on a time percentage basis, for quadriceps and hamstring during ascending stairs. Each of the FIGS. 3A-3C depicts one cycle. While the duration of one cycle may vary, the pattern remains the same as stimulation is applied to each of the opposed muscle groups.

Figure 4:
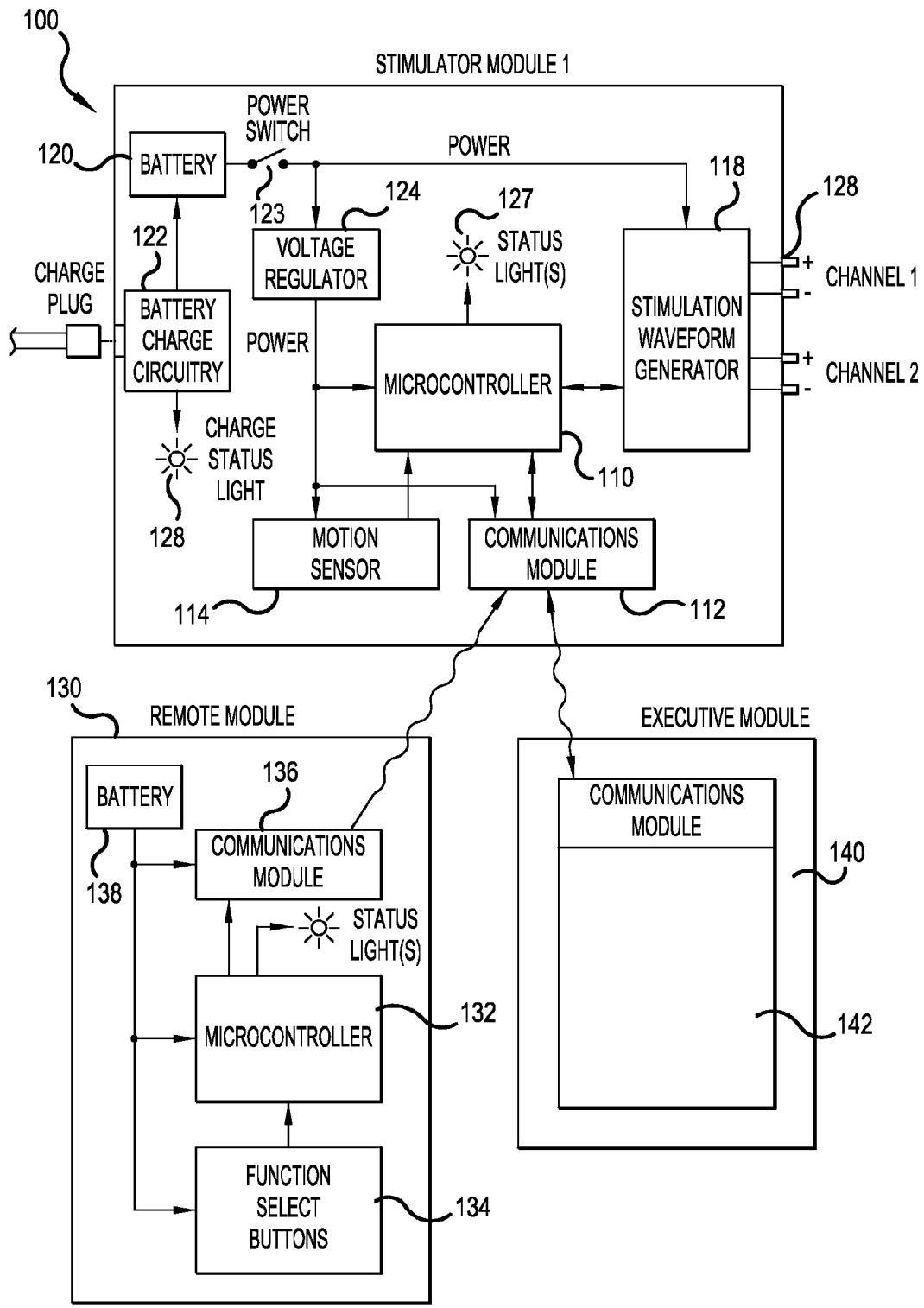
FIG. 4 is a block diagram of the system.

The system of the present invention is shown in FIG. 4. The stimulator module 100 provides dual-muscle stimulation via two electrical output channels (Channel 1 and Channel 2)

128. Each channel has positive and negative output pulses delivered to the body via non-invasive (surface) electrodes 151-154 attached to the body (over the target muscle group). A battery 120 provides the electrical energy to run the stimulation module. A removable wall-powered Charge Plug and Battery Charge Circuitry 122 recharge the battery. A status light 125 provides the charging status. A Power Switch 123 controls power to all circuits in the Stimulator Module, except for the Battery charger. A Voltage Regulator 124 provides a clean and regulated direct current voltage which provides power to the Microcontroller 110, motion sensor 114 and Communications Module 112. The Status Light 127 provides On/Off, Stimulation and Error Status of the Stimulator Module.

Any suitable device can be used as the Microcontroller 110, such as a single chip computer to control the Stimulator Module in performing the desired functions. The Microcontroller 110 stores different stimulation patterns, gathers inputs from the motion sensor 114 and Communications Module 112 and controls the Stimulation Waveform Generator 118 to provide the desired stimulation output. The Stimulation Waveform Generator 118 has a voltage booster, such as an inductor, to generate the voltage required to cause current flow in the circuit. The Output Channel Switches 128 apply the desired different waveforms to the electrodes. The different waveforms include rectangular shape monophasic, rectangular shape triple monophasic, geometrically symmetric rectangular shape biphasic with intra-pulse interval (IPI), and geometrically symmetric rectangular shape triple biphasic with intra-pulse intervals. All functions are monitored and controlled by the Microcontroller.

The motion sensor 114 detects movement, pressure, sound, position and acceleration of a specific area of the body. The motion sensor may be used as a trigger to initiate the waveform generator to output a signal, as will be explained in more detail later. The Communications Module 112 receives configuration data and transmits performance information (telemetry) to the Executive Module 140. The communications link with the Executive Control unit 140 is bidirectional, allowing full control, configuration, status and telemetry data exchange.

The Remote Module 130 is a small handheld control unit providing On/Off, Mode and stimulation level control of the Stimulation Module 100. This unit is the main control interface for the patient (user). The Communications Module 136 can be any suitable device, such as a low power, radio frequency transmitter and communication is achieved in any suitable fashion, such as a one way radio frequency link from the Remote Module 130 to the Stimulator Module 100. A battery 138 provides the electrical energy to operate the Remote Module 130. Due to the low power demands, the battery 138 can be a primary (non-rechargeable) type. A Status Light provides verification that function buttons have been pushed and that the corresponding command has been transmitted to the Stimulator Module 100. The Microcontroller 132 detects the activation of the Function Select buttons 134, and sends the corresponding command to the Communication Module 136 for transmission to the Stimulation Module 100. The Microcontroller can be any suitable device, such as a single chip computer The Executive Control device provides the desired operational interface for the clinician. The Executive Control 140 provides the primary method for a clinician to configure and customize the Stimulator Module 100 for each patient (user). The Executive Control 140 can be any type of personal or handheld computer device, such as a desktop, laptop, notebook, tablet, personal digital assistant (PDA) or Smart Phone, which has the capability to communicate with the Stimulator Module 100 or a suitable external port (USB, Serial, etc.) to support a compatible radio frequency transceiver. With a bidirectional radio frequency data link, the clinician can observe and adjust the stimulation parameters in real time to yield the most effective patient treatment. The Executive control 140 can be used to configure and customize an unlimited number of Stimulator modules 100. The Communications Module 142 has a bi-directional radio frequency transceiver which may be already present in the computer or externally connected.

A three dimensional motion sensor 114 is used as the trigger mechanism so that any detected motion acts as a trigger to cause the microcontroller 110 to have the stimulator waveform generator to output the appropriate stimulation pattern to create the desired motion. Any suitable motion detector may be used, such as a tri-axial accelerometer, a gyroscope or a magnetometer. In addition, pressure or sound sensors within the stimulator can be used as a trigger. A single motion, pressure or sound detector (collectively termed sensor) embedded in the stimulator electronic circuit enables the activation of two or more muscle groups at the correct time regardless of the cadence (the number of steps taken per minute) for each patient. By using a motion sensor, the trigger mechanism is not based on a mechanical force, such as foot switches/sensors. Eliminating mechanical foot sensors removes material fatigue, sensor degradation, and pressure sensitivity issues. Thereby, an inexpensive and simple motion sensor provides a more accurate and reliable trigger mechanism.

As an example, a single motion sensor trigger provides accurate timing of activation for the key muscles controlling the ankle (dorsiflexors and plantar flexors), the knee (quadriceps and hamstrings), the hip (abductors and extensors), and the trunk (back and abdominal muscles). In addition to triggering the activation of two or more muscle groups during a proper walking sequence, the motion sensor also determines walking vs. stair negotiation; sit to stand, and non-walking status of the patient. Thus, the system can turn the stimulation "on" when the user is walking or practicing other locomotor activities and turn the stimulation "off" when the user is standing, sitting, or otherwise at rest. This enables the patient to wear the device throughout the day and receive stimulation only when needed. This also provides a system which prolongs battery life.

Figure 5:
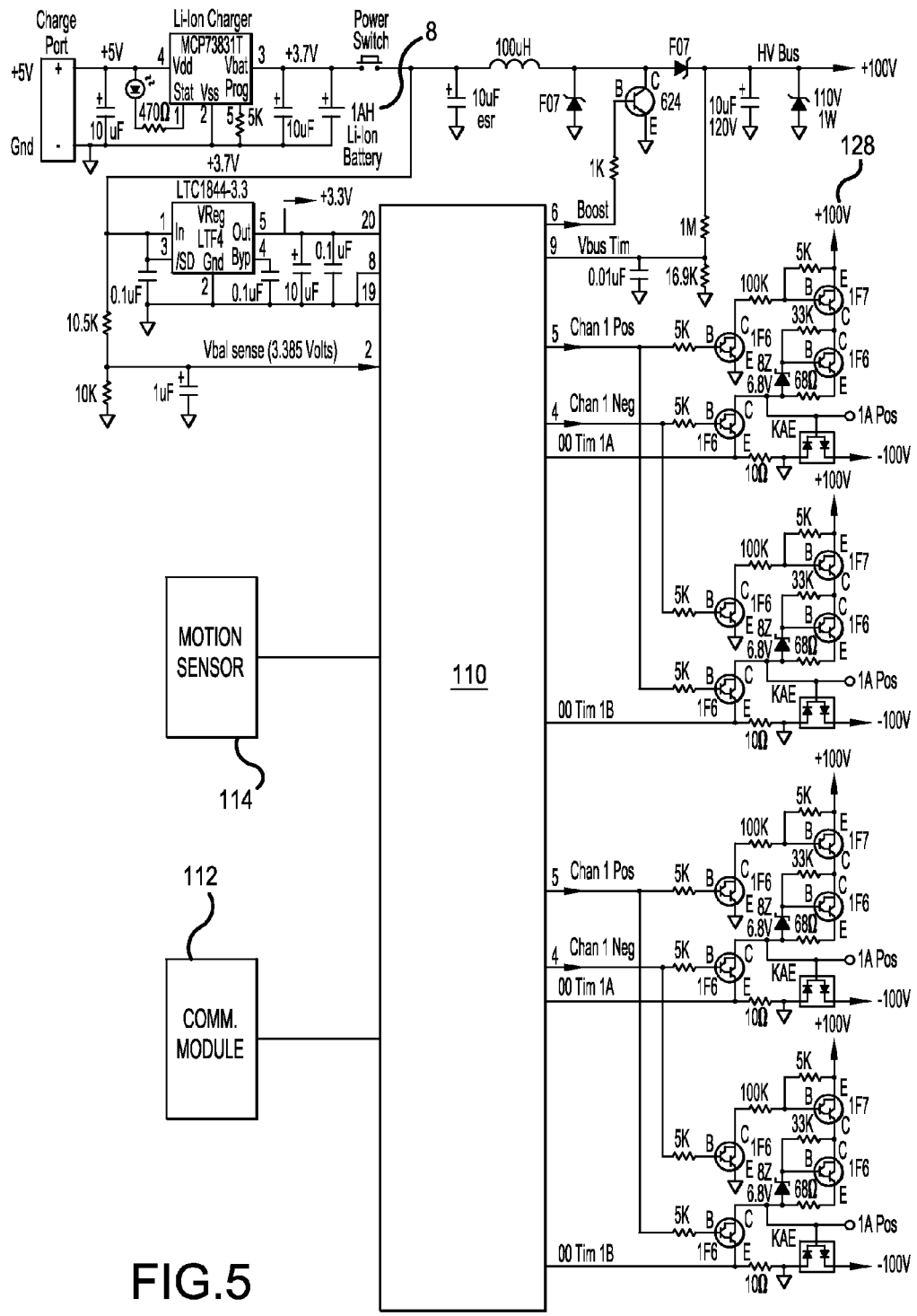
FIG. 5 is a schematic diagram of the stimulator module.
Figure 6A:
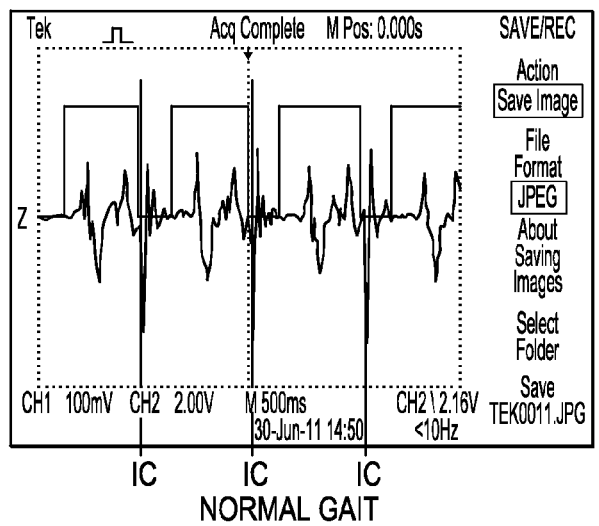
FIGS. 6A-6E are graphs comparing sensor outputs for a motion sensor and a force sensor.
Figure 6B:
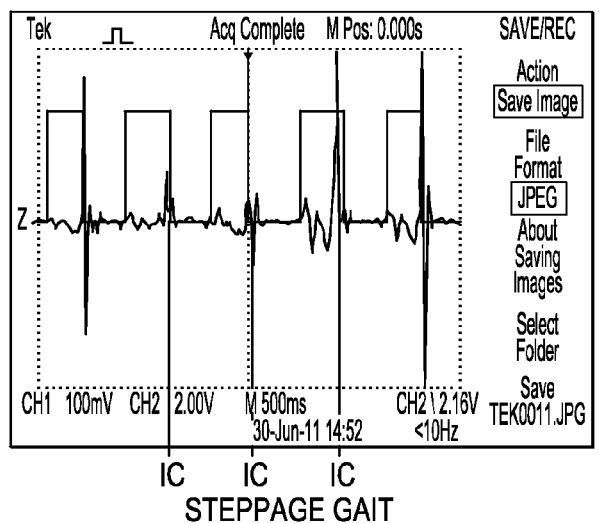
Figure 6C:
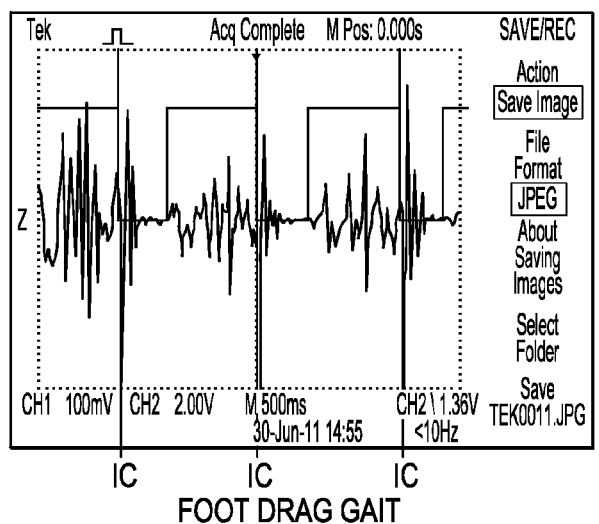
Figure 6D:
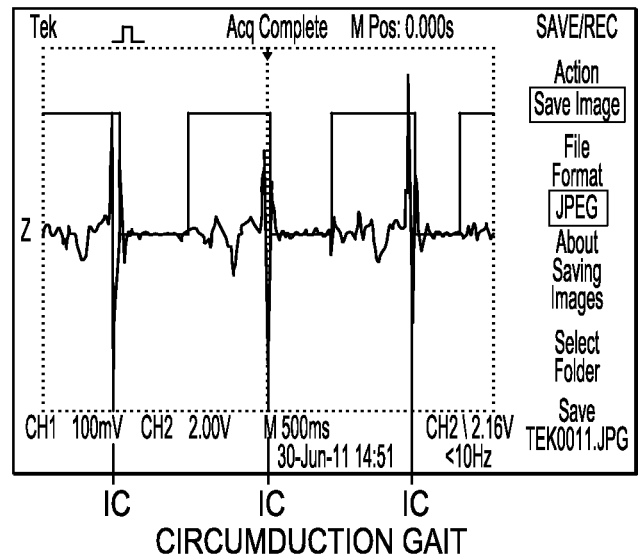
Figure 6E:
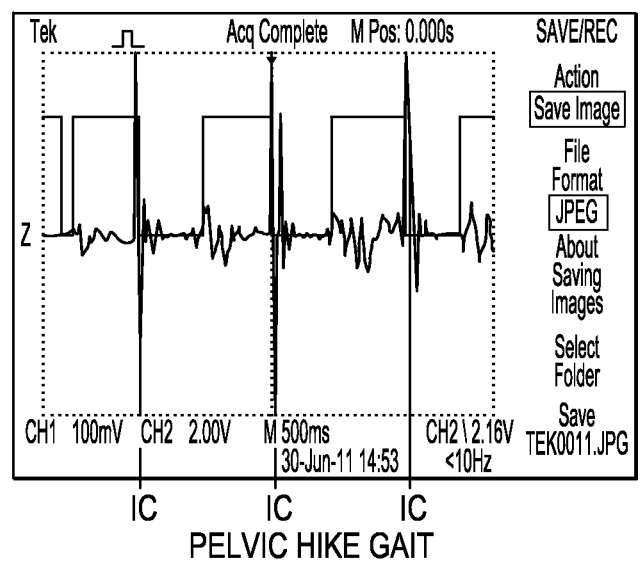

FIG. 5 depicts the components in the Stimulation Module 100. All components communicate with the microcontroller 110. The motion sensor may be a tri-axial accelerometer, gyroscope, magnetometer, pressure, or sound sensor as previously mentioned. The communication module also may be any suitable device, such as a Blue-tooth module and RF receiver. The voltage is supplied to the electrical output channels 128. The circuitry for the power supply utilizes an inductor, instead of a transformer, to reduce overall size and weight of the device.

The waveform generator provides constant current by using a zener diode in the waveform generator 118. The use of constant current, as opposed to constant voltage, results in complete control of the charge per phase (commonly termed phase charge) delivered to the stimulated muscles, thus enabling to minimize the phase charge needed to induce contraction leading to a more comfortable experience for the user. This is because the electrical impedance (opposition to current flow in a biological conductive medium) varies greatly depending on the impedance of the user's skin and subcutaneous tissues, which varies due to many factors, such as the moisture level of the skin. In a constant voltage system, the electric current (and phase/pulse charge) varies widely and needs to be adjusted constantly to provide the same level of comfort to the user. As noted earlier, the stimulation waveform generator can create different waveforms, including rectangular shape monophasic, rectangular shape triple monophasic, geometrically symmetric rectangular shape, biphasic pulse with intra-pulse interval (IPI) and geometrically symmetric rectangular shape, triple biphasic pulse with intra-pulse interval (IPI). Geometrically symmetric, rectangular shape is one critical key in minimizing the phase charge needed to induce contraction of skeletal muscles.

Figure 8A:
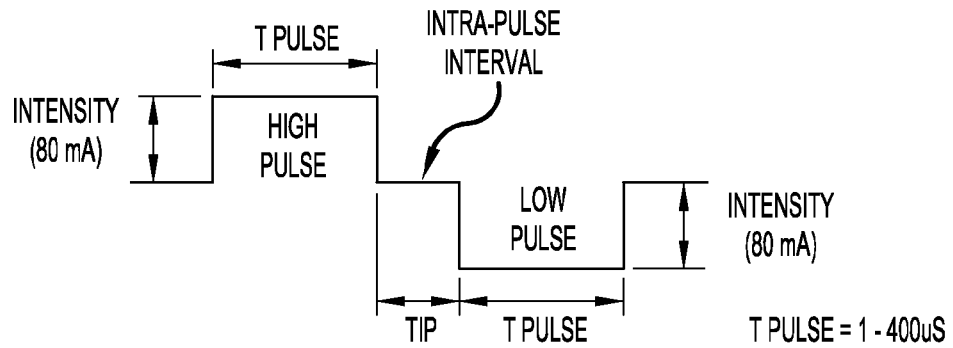
FIGS. 8A-C depict different waveforms that can be generated by the waveform generator.
Figure 8B:
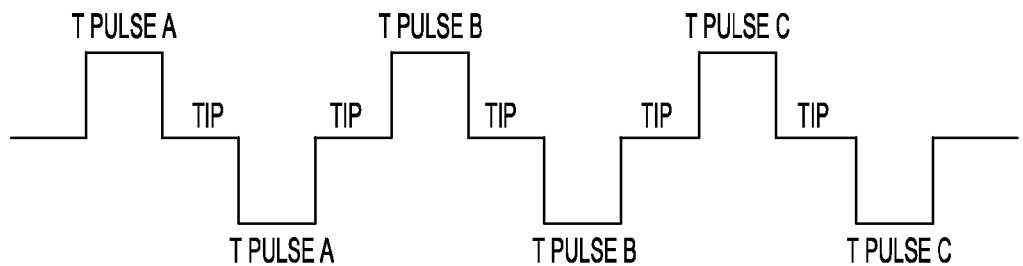
Figure 8C:
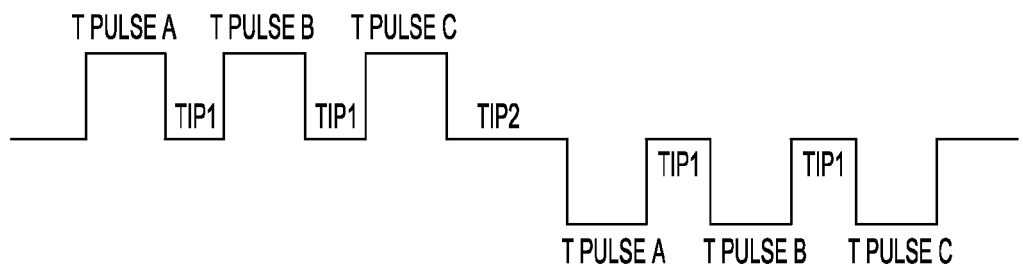

FIG. 8A depicts a symmetrical biphasic waveform having an intensity of 80 mA, where $T_{ip}$ is 100 μS and $T_{pulse}$ is between 1-400 μS, where the exact duration of $T_{pulse}$ is determined by the method described above. FIG. 8B depicts a triple biphasic waveform. Again, $T_{ip}$ is 100 μS and $T_{pulse}$ is between 1-400 μS. FIG. 8C depicts a triple Positive/Triple Negative waveform where $T_{ip1}$ is 30 μS, $T_{ip2}$ is 100 μS and $T_{pulseX}$ is 1-400 μS.

Two modes of stimulation are utilized. First, the system will stimulate two or more synergistic muscle groups during walking or other locomotor activities (walking mode). Second, based on the desired application, the system provides electrical stimulation to the muscles at the correct timing sequence for normal walking or other locomotor activities even when the patient is not walking (termed simulation mode). This simulation mode will electrically stimulate the muscles without dependence on the motion sensor, to help the user train and control the muscles even if he/she are unable to walk. Further, this mode will help individuals experience the proper timing for muscle activation and joint movements thereby helping the central nervous system re-learn the timing sequence for walking or other locomotor activities, even if unable to walk for a period of time.

The present system can be pre-programmed to provide stimulation at the correct time for many movements in the lower body (ankle dorsiflexion and plantar flexion, knee extension and flexion, hip extension, and hip abduction and adduction). In addition, the present system can be programmed to stimulate other muscles in the body such as abdominals, back extensors, or upper extremity muscle groups during walking and other activities of daily living such as lifting and carrying objects. The timing of electrical stimulation to the appropriate muscle group to achieve the desired action, such as sit to stand or lifting, are well known through published studies in movement science literature.

In addition, the software controlling the timing of the electrical stimulation triggered by the motion sensor can automatically adjust the timing based on the actual performance of each individual user. Specifically, the system of the present invention is designed to electrically induce contraction in desired muscles at the correct time during walking. Timing for stimulation for each stride is triggered by a motion sensor, such as a single tri-axis accelerometer, incorporated with the infrastructure of the stimulator affixed to the body, often on the lower leg or upper leg (also termed thigh) for walking. Software collects and determines acceleration and deceleration data from the sensor to precisely determine when the user is beginning each stride (called initial contact—IC). FIG. 6 depicts sensor outputs for normal gait and for four common abnormal gaits. In FIG. 6, the wavy line represents IC from an accelerometer and the square wave line represents a heel switch during gait (walking patterns). Due to the mechanical delay inherent in foot sensor technology, the motion sensor data are more accurate for defining IC. As can be seen, the motion sensor is able to detect all initial contacts that the heel switch sensor detected. The motion sensor is able to detect the initial contact even when having a continuous output. Software within the system detects time between initial contacts and can adjust the cycle time from a default setting to the actual cycle time obtained during walking and continue to adjust it as the user increases or decreases walking speed.

From the motion sensor data, the software identifies two consecutive IC data points and calculates the duration of the stride. Based on the duration, the desired muscle pattern calculated as percentage activation during walking, stimulation is provided to the muscle at the next stride. Thus, timing for the electrical stimulation for each stride is based on the previous stride. FIG. 3A shows the desired timing for the dorsiflexor and plantar flexor muscles based on a normal walking cycle. Regardless of the cadence (steps per minute) or speed (distance per minute), the software calculates the duration for each stride (from IC to IC) and provide stimulation of the muscles (in this example dorsiflexors and plantar flexors) at the correct percentage of the next stride. The stimulation starts upon detection of the first IC and uses default (pre-programmed) stride duration for the first stride.

The system software uses the motion sensor data to determine when the stimulation is applied ON condition vs. OFF condition. The walking mode will be activated ON when the user is walking; and deactivated OFF when the user is standing, sitting, or otherwise at rest. The built-in software has an adjustable timer which is used to control this function. The timer detects how long it has been since the last IC occurred and when a pre-programmed time interval is reached, the stimulation is halted. The stimulation will remain paused until an IC is detected, at which point the stimulation will resume. The pre-programmed time interval may be adjusted by a clinician. In the simulation mode, the software system provides stimulation for the desired muscles at the correct time for walking, or other locomotor activities, even when the patient is sitting, standing, or otherwise at rest. The desired muscle group(s) to be stimulated is selected and data to stimulate these muscle group(s) are entered. The software provides a "default setting" for many major muscle groups in the body. This setting will provide the normal timing pattern for the user based on published studies in movement science literature. The software also provides an "advanced setting." In this setting the clinician can determine desired timing for the stimulation for a specific muscle based on their clinical expertise, judgment, and desired therapeutic goal.

It is a well-known electrophysiological phenomenon that the electrical variable termed phase charge (mathematically calculated as the current-time integral) will determine, within limits, whether a peripheral nerve will or will not be excited.

The electrical impulse provided by the system increases the intensity of stimulation by increasing the phase duration of the pulse while having a fixed maximal peak current in order to minimize the phase charge needed to induce muscle contraction and thus significantly increase comfort of stimulation. Typical FES systems increase the intensity of stimulation by increasing the current amplitude at pre-selected phase duration and by doing so, injecting unnecessarily high phase and pulse charges that increase the discomfort of the stimulation. The present system minimizes the phase charge needed to induce contraction in very small and very large muscle sizes, and achieve the full spectrum, from very weak to very strong contraction. As a result the entire stimulation system can be miniaturized including battery size and therefore weighs much less than existing stimulators, and can be manufactured as an aesthetic, wearable, very comfortable self-administered system.

Figure 7:
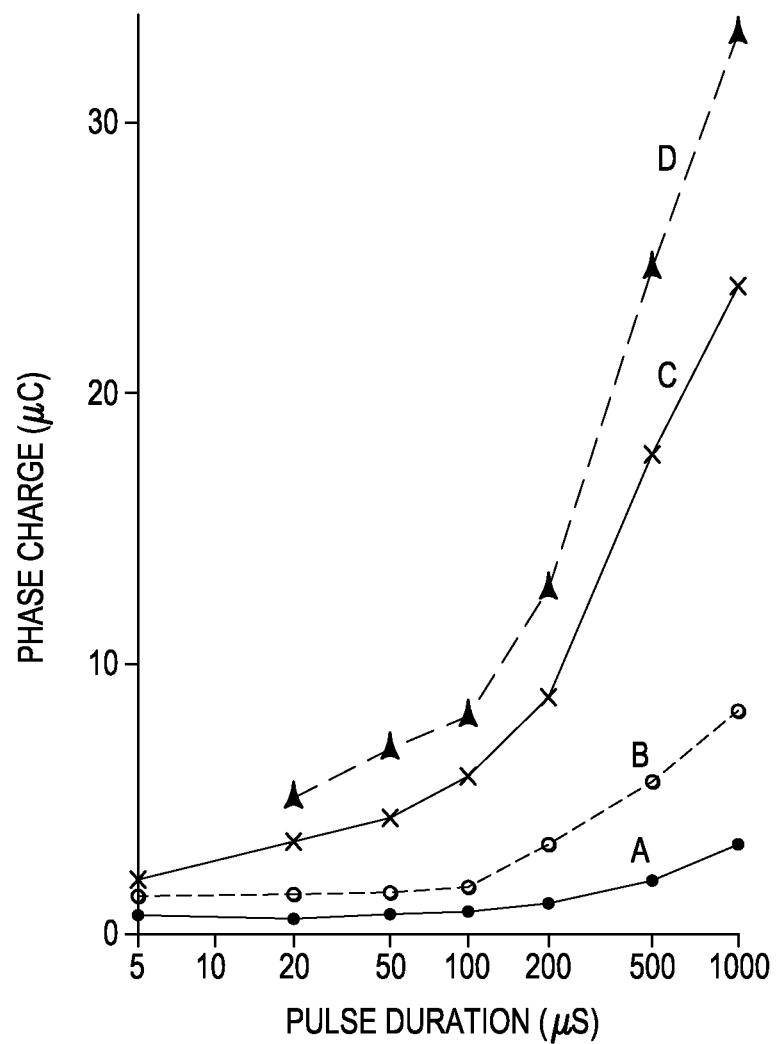
FIG. 7 is a graph of the relationship between phase charge and pulse duration.

The relationship between phase duration and phase charge are illustrated in FIG. 7, where line A denotes the threshold for feeling an impulse, usually as a tingling sensation. Line B denotes the intensity needed to cause muscular contraction, line C denotes the threshold for feeling (perceiving) pain and line D denotes the threshold for maximal pain tolerance. As can be seen, the shorter the duration the less the charge necessary to excite sensory and motor nerves. The reason for requiring less charge to discharge the peripheral nerves is derived from the known electrophysiological phenomenon that the shorter the pulse/phase duration, the less the impedance.

Traditionally, most stimulators are designed to increase phase (also termed pulse in the literature) charge by pre-determining (setting up) the phase/pulse durations and increasing the current (mA) and voltage (V) amplitude, also termed "intensity," to a generate phase charge sufficient to excite the sensory and motor nerves leading to muscle contraction. As can be seen in FIG. 7, setting up phase duration in the range of 50-400 microseconds (as is the circuit design of most battery powered stimulators) requires considerable increase in phase charge to effectively induce contraction of skeletal muscles.

In the present invention, the peak current (mA) is pre-determined and sufficient phase charge is generated by always increasing the phase duration from the shortest duration (0.5-1 microsecond) to the longest duration necessary to induce the desired muscle contraction. Using such an approach results in requiring a much shorter phase duration to excite the sensory and motor nerves. As a result, the muscle contraction is perceived by the user to be considerably more comfortable than other electrical stimulation systems. Furthermore, the system described by the present invention enables to deliver the proper phase charge, by pre-determining the peak current based on the size of the muscle and the desired level of contraction. As a result, the phase charge needed to obtain effective contraction is reduced considerably compared to existing stimulators.

Using the approach outlined above, the stimulation is much more comfortable, with less charge and charge density. Electro-physiologically, a very short phase duration delay excitation of nerve fibers (afferent input) perceived as painful stimulation. There is also less likelihood of causing skin irritation. In addition, energy consumption is reduced considerably, allowing the use of a smaller battery, further miniaturizing the stimulator, and reducing the weight of the system. This approach also eliminates a key stimulus control that commercially available stimulators are required to have (increasing peak current [mA] and voltage) and also simplifies circuit design. Thus, the operation of the stimulator by users (clinicians and patients) is markedly simplified. The presence design also enables the use of any electrode size without "maxing out" the stimulator output.

Modifications of the method and system of the present system will likely occur to those who have had the benefit of the foregoing disclosure. For example, the signals from the foot switches to the module could be transmitted wirelessly instead of through electrical conductors. The module used in either or both of the unilateral and bilateral embodiments of the system may incorporate, within a unitary housing, an electrical stimulator, a motion detector and on/off controller, a single power source for all of the powered units, and a single micro-controller providing logic controls for the electrical stimulator and the on/off controller.

What is claimed is:

1. A non-invasive, wearable electrical stimulator which consists essentially of
   a controller,
   a motion sensor in electrical communication with the controller and adapted to detect a beginning and end of cycles of locomotion activity, wherein the motion sensor does not include foot switches,
   a power source, and
   a constant current waveform generator receiving power from the power source and controlled by the controller, wherein the controller, motion sensor, power source and waveform generator are contained in a singular housing adapted to be worn on a body part of a user, and
   a plurality of electrodes adapted to apply electrical stimulation in a timed stimulation pattern to multiple, different muscle groups of the user which contract synergistically and cooperate together to stimulate complete cycles of locomotion activity, said plurality of electrodes electrically connected to the waveform generator for supplying electrical stimuli to nerves and muscles of the user sufficient to cause timed contraction of the different muscle groups required for achieving each complete cycle of locomotion activity,
   wherein the motion sensor functions to recognize the initiation of different complete cycles of locomotion activity which acts as a trigger for the electrodes to deliver the electrical stimulation to appropriate muscles of the multiple, different muscle groups to be active in each of the different locomotion activity cycles, at a time when the appropriate muscles of the multiple different muscle groups need to be activated to achieve each different locomotion activity cycle, said electrical stimulation being synchronized with each of the different complete cycles of locomotion activity and applied throughout an entire cycle of each of the different complete cycles.

2. The electrical stimulator of claim 1, further comprising a zener diode in the waveform generator.

3. The electrical stimulator of claim 1, wherein the power source includes an inductor.

4. The electrical stimulator of claim 1, wherein the motion sensor is one of a tri-axial accelerometer, a gyroscope, a magnetometer, and a pressure or sound sensor.

5. The electrical stimulator of claim 4, wherein the motion sensor enables activation of a plurality of different muscle groups at a correct timing sequence, regardless of a cadence of the user for repeatably achieving a desired complete cycle of locomotion activity.

6. The electrical stimulator of claim 4, wherein the motion sensor defines a dual-purpose trigger mechanism which turns the stimulator on when the user is walking or practicing other cyclical locomotion activity including repeatably standing up and sitting down, lifting, moving and placing objects and off when the user stops walking or stops repeating the other locomotion activities.

7. The electrical stimulator of claim 1, wherein the waveform generator outputs one of a monophasic, a triple monophasic, geometrically symmetric biphasic with intra-pulse interval and triple geometrically symmetrical biphasic with intra-pulse intervals waveform.

8. The electrical stimulator of claim 1, wherein the waveform generator is configured to generate a waveform with an adjustable phase duration and a fixed maximum peak current to minimize a phase charge needed to induce muscle contraction.

9. The electrical stimulator of claim 1, further comprising a remote control unit operatively communicating with the electrical stimulator and configured to allow adjustment of an intensity of the stimulus power (charge) output and to activate the waveform generator.

10. The electrical stimulator of claim 1, further comprising a wireless executive control unit which is operatively communicating with the controller to enable a clinician to selectively initiate a stimulation cycle to be provided to the electrodes to increase or decrease an intensity of the stimulation and other parameters, including pulse rate and to alter the electrical stimulation created by the electrical stimulator.

11. The electrical stimulator of claim 1, wherein the cycle of locomotion activity is walking with a defined gait of a user and the electrical stimulation of the different muscle groups is correctly timed to be activated when needed throughout the gait cycle.

12. The electrical stimulator of claim 11, wherein the motion sensor detects a cycle time of the gait and is adapted to adjust timing of the stimulation from a default setting to the detected cycle time established by the gait, with continual adjustment as the user increases or decreases gait cycle speed.

13. The electrical stimulator of claim 1, wherein the cycle of locomotion activity includes a repeating standing up to sitting down cycle, walking cycle, stair climbing cycle and lifting and moving objects from one location to another.

14. The electrical stimulator of claim 1, wherein the motion sensor is adapted to turn itself on and off.

15. The electrical stimulator of claim 1, wherein said stimulator is adapted to create different timed stimulation patterns and cycles depending on a particular, different synergistically coupling of muscle groups to which the electrodes are applied for performing the desired cycles of locomotion activity.

16. The electrical stimulator of claim 1, which comprises two electrical output channels electrically coupling to the plurality of electrodes to the constant current waveform generator for providing dual-muscle stimulation for targeted muscle groups.

17. The electrical stimulator of claim 1, wherein the electrical stimulation generates an electrical impulse which increases an intensity of the stimulation by increasing a phase duration of the impulse while maintaining a fixed maximal peak current in order to minimize a phase charge needed to induce muscle contraction and increase a comfort level of electrical stimulation.

18. The electrical stimulator of claim 1, wherein the stimulation timing pattern is a defined pattern which can be automatically modified to conform to an actual pattern of the muscle contractions in performing the different cycle of locomotion activity.

19. The electrical stimulator of claim 1 wherein the different muscle groups include the dorsiflexors and plantar flexors, abdominals and back extensors, quadriceps and hamstrings, hip abductors, hip adductors and hip extensors.

20. The electrical stimulator of claim 1, wherein the initiation of the cycle locomotion activity activates the motion sensor as a result of contact of a body part of the user with a surface.

21. The electrical stimulator of claim 20, wherein the surface is the ground, a floor, or a chair.

22. The electrical stimulator of claim 1, wherein cycle of the locomotion activity corresponds to the user's demands or to a predetermined cycle time for each particular cycle of locomotion activity.

23. The electrical stimulator of claim 1, further comprising a remote control unit operatively communicating with the controller and configured to induce timely muscle contraction which coincides with a complete cycle of locomotion activity, without volitional participation of the user in activation of target muscles.

24. The electrical stimulator of claim 1, further comprising an executive control unit operatively communicating with the controller and configured to enable a clinician to induce timely muscle contraction which coincides with a complete cycle of locomotion activity without volitional participation of the user in activation of target muscles.

25. The electrical stimulator of claim 1, which further comprises a remote control unit operatively communicating with the controller and configured to induce timely muscle contraction in a timed stimulation associated with a complete cycle of locomotion activity which functions to modulate the central nervous system of the user to replicate the complete cycle of locomotion activity.

26. The electrical stimulator of claim 1, which further comprises an executive control unit operatively communicating with the controller and configured to induce timely muscle contraction in a timed stimulation associated with a complete cycle of locomotion activity which functions to modulate the central nervous system of the user to replicate the complete cycle of locomotion activity.

* * * * *